(12) United States Patent
Reinhorn et al.

(10) Patent No.: US 9,076,632 B2
(45) Date of Patent: Jul. 7, 2015

(54) POSITION SENSITIVE STEM DETECTOR

(71) Applicant: EL-MUT TECHNOLOGIES LTD., Rehovot (IL)

(72) Inventors: Silviu Reinhorn, Mevaseret Zion (IL); Eli Cheifetz, Ramat Gan (IL); Amit Weingarten, Ramat Gan (IL)

(73) Assignee: EL-MUL TECHNOLOGIES LTD., Rehovot (IL)

( * ) Notice: Subject to any disclaimer, the term of this patent is extended or adjusted under 35 U.S.C. 154(b) by 0 days.

(21) Appl. No.: 14/378,098

(22) PCT Filed: Feb. 12, 2013

(86) PCT No.: PCT/IL2013/000015
§ 371 (c)(1),
(2) Date: Aug. 12, 2014

(87) PCT Pub. No.: WO2013/118111
PCT Pub. Date: Aug. 15, 2013

(65) Prior Publication Data
US 2015/0034822 A1 Feb. 5, 2015

Related U.S. Application Data

(60) Provisional application No. 61/597,792, filed on Feb. 12, 2012, provisional application No. 61/607,178, filed on Mar. 6, 2012.

(51) Int. Cl.
*H01J 37/26* (2006.01)
*G01T 1/20* (2006.01)
(Continued)

(52) U.S. Cl.
CPC ................. *H01J 37/28* (2013.01); *G01N 23/04* (2013.01); *H01J 37/244* (2013.01);
(Continued)

(58) Field of Classification Search
CPC ............ H01J 2237/2443; H01J 37/244; H01J 2237/221; H01J 2237/2445; H01J 2237/26; H01J 2237/2802; G01T 1/2018
USPC ............. 250/311, 310, 307, 306, 397, 370.11
See application file for complete search history.

(56) References Cited

U.S. PATENT DOCUMENTS 5,729,584 A  3/1998  Moorman
6,640,014 B1 10/2003 Price et al.
(Continued)

FOREIGN PATENT DOCUMENTS

JP            02220339          3/1990

OTHER PUBLICATIONS

N. Shibata, Y. Kohno, S.D. Findlya, H. Sawada, Y. Kondo, Y. Ikuhara, "New area detector for atomic-resolution scanning transmission electron microscopy," Journal of Electron Microscopy, 59(6): 473-479 (2010).

*Primary Examiner* — Nikita Wells
(74) *Attorney, Agent, or Firm* — Daniel J. Swirsky; AlphaPatent Associates Ltd.

(57) ABSTRACT

A STEM system is disclosed wherein an imaging system is used to image the electron scatter pattern plane of the HAADF detector onto a two-dimensional array detector. A data acquisition system stores and processes the data from the two-dimensional array detector. For each illumination pixel of the STEM, one frame of data is generated and stored Each frame includes data of all scattered angles and can be analyzed in real time or in off-line at any time after the scan. A method is disclosed for detecting electrons emitted from a sample by detecting electrons scattered from the sample and generating plurality of corresponding signals, each signal indicative of scattering angle of a scattered electron; generating a plurality of signal groups, each signal group being a collection of signals of a user selected scattering angle.

20 Claims, 14 Drawing Sheets

(51) Int. Cl.
*H01J 37/28* (2006.01)
*H01J 37/244* (2006.01)
*G01N 23/04* (2006.01)

(52) U.S. Cl.
CPC . *H01J 2237/2445* (2013.01); *H01J 2237/2446* (2013.01); *H01J 2237/26* (2013.01); *H01J 2237/221* (2013.01); *H01J 2237/2443* (2013.01); *H01J 2237/2802* (2013.01); *H01J 2237/2806* (2013.01)

(56) References Cited

U.S. PATENT DOCUMENTS

| | | | |
|---|---|---|---|
| 7,045,781 | B2 | 5/2006 | Adamec et al. |
| 7,126,687 | B2 | 10/2006 | Hill et al. |
| 7,227,144 | B2 * | 6/2007 | Tsuneta et al. ............ 250/311 |
| 7,372,029 | B2 | 5/2008 | Tsuneta et al. |
| 7,439,502 | B2 | 10/2008 | Nakasuji et al. |
| 7,470,915 | B2 | 12/2008 | Slowko |
| 8,017,913 | B2 | 9/2011 | Zhevelev et al. |
| 2007/0206203 | A1 * | 9/2007 | Trainer ..................... 356/521 |
| 2008/0221814 | A1 | 9/2008 | Trainer |
| 2009/0174935 | A1 | 7/2009 | Szulczewski |
| 2010/0038534 | A1 | 2/2010 | Hendrich |
| 2010/0231911 | A1 | 9/2010 | Fischer |
| 2010/0328746 | A1 | 12/2010 | Daquino |
| 2011/0057121 | A1 | 3/2011 | Yang |
| 2011/0133055 | A1 | 6/2011 | Andrews |
| 2011/0278451 | A1 | 11/2011 | Tiemeijer |
| 2012/0025074 | A1 * | 2/2012 | Barbi et al. ............... 250/307 |
| 2013/0032713 | A1 * | 2/2013 | Barbi et al. ............... 250/307 |

* cited by examiner

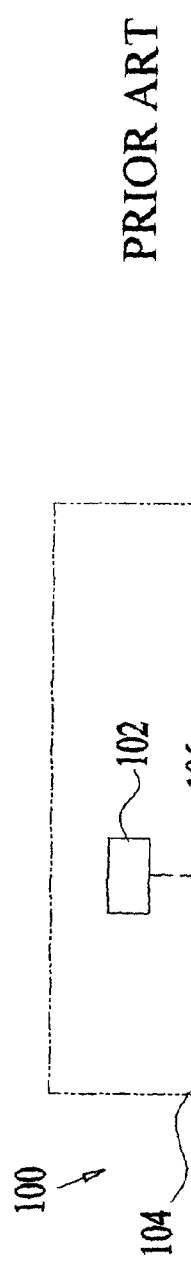
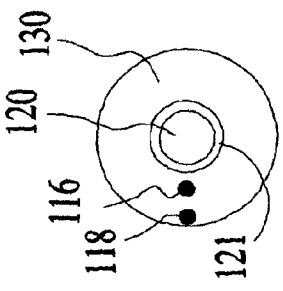
FIG. 1B
FIG. 1A
PRIOR ART

POSITION SENSITIVE STEM DETECTOR

CROSS-REFERENCE TO RELATED APPLICATIONS

This application is a U.S. National Phase Application under 35 U.S.C. 371 of International Application No. PCT/IL2013/000015, which has an international filing date of Feb. 12, 2013, and which claims priority benefit from U.S. Provisional Patent Application No. 61/597,792, filed Feb. 12, 2012, and from U.S. Provisional Patent Application No. 61/607,178, filed Mar. 6, 2012, the disclosures of both of which are incorporated herein by reference in their entirety.

RELATED APPLICATIONS

This application claims priority benefit from U.S. Provisional Application Ser. No. 61/597,792, filed Feb. 12, 2012, and from U.S. Provisional Application Ser. No. 61/607,178, filed Mar. 6, 2012, the disclosures of both of which are incorporated herein by reference in their entirety.

BACKGROUND

1. Field

This invention relates generally to Transmission Electron Microscope (TEM) and, more particularly, to Scanning Transmission Electronic Microscope (STEM).

2. Related Art

Transmission electron microscope (TEM) is a system which transmits a beam of electrons through a very thin specimen. An image of the area of the specimen illuminated by the beam is formed from the electrons exiting the other side of the specimen. A scanning transmission microscope (STEM) is a system wherein the electron beam is focused to a point and is scanned over a selected area of the specimen. TEM systems having the appropriate additional parts may operate in either TEM or STEM modes; however, dedicated STEM systems are also available.

FIG. 1A is a simplified sectional illustration of a conventional TEM system 100, that may operate in either TEM or STEM mode. As seen in FIG. 1A, a conventional TEM/STEM system 100 comprises an electron beam column 102 within a vacuum chamber 104. The electron beam column 102 emits an electron beam 106, which is focused using conventional electron optics (not shown) for scanning a sample 110 during the scanning mode of the TEM/STEM system 100. A relatively large amount of the electrons pass directly through the sample 110. Some electrons 114 are scattered by the sample 110 following impingement of the electron beam 106 thereon. It is known in the art that the number of scattered electrons and the distribution of the scattering angle θ are related to the atomic number Z of a scanned atom within the sample 110 and to the thickness of the sample. As seen in FIG. 1A, a relatively small number of scattered electrons with a relatively small scattering angle $\theta_1$ of scattered electrons 116 indicate that the atomic number of the scanned atom is relatively small and/or that the sample is thin at that scanning location. Similarly, a relatively large number of scattered electrons with a relatively large scattering angle $\theta_2$ of scattered electrons 118 indicate that the atomic number of the scanned atom is relatively large and/or that the sample is thick at that scanning location. Thus, information regarding the composition of the atomic numbers of the atoms in the scanned sample may be determined by the number of electrons that undergo scattering and the distribution of the scattering angles. However, accurate determination is sometimes difficult due to the signal contribution from the thickness of the sample.

A standard Bright Field detector 120 may be used to detect the un-scattered electrons passing through the sample 110 or detect electrons with a relatively low scattering angle. The Bright Field detector 120 is typically formed of a silicon-diode detector, suitable mainly for detecting un-scattered electrons or scattered electrons with a relatively small scattering angle. The signal obtained from the bright field detector is used to generate an image of the sample which conveys the physical structure of the sample, but not the atomic composition of the sample.

One or two annular detectors are usually provided for detecting scattered electrons in the STEM mode of operation. An Annular Dark Field (ADF) detector 121 for smaller scattering angle electrons and a High Angle Annular Dark Field (HAADF) detector 130 for a range of larger scattering angle electrons may be provided. The dark field detectors can be used to obtain information about the atomic composition of the sample. The ADF detector for smaller angles and relatively high number of scattered electrons may be a silicon diode detector or a scintillator based detector. The silicon diode detector performance is limited by the relatively high dark current noise and low amplification. Thus it is suitable for a relatively high signal operation mode where the total current impinging on the silicon diode is higher than 10 pA (Pico-Ampere). The ADF detector 121 may be an annular detector provided about the bright field detector 120, as shown in the example of FIG. 1A.

The HAADF is typically a scintillator based detector, which is suitable for detecting scattered electrons emitted from the sample 110, wherein the electron beam current is not high. As seen in FIG. 1A, a HAADF detector assembly comprising a scintillator based detector assembly 130 is provided for detecting the scattered electrons emitted from the sample 110. The scintillator based detector assembly 130 comprises a scintillating surface 134 formed of a scintillating material, such as YAP, YAG, or a layer of phosphorous scintillating material such as P47 or R42, for example. The scintillating surface 134 is formed with an aperture 140 for allowing the un-scattered electrons to pass through to the Bright Field detector 120 and the ADF detector 121 if used. Upon impingement of an electron 114 on the scintillating surface 134, a light signal 142 is formed and guided by a light guide 144 to a Photomultiplier Tube (PMT) 150 and impinges thereon. The scintillator based detector assembly 130 may be coupled to a retracting mechanism 184, which is provided to retract the scintillator based detector assembly 130 from the electron beam path wherein the scintillator based detector assembly 130 is not in operation, such as during a TEM detection mode.

Turning to FIG. 1B, which is a simplified sectional illustration taken along lines IB-IB in FIG. 1A, a top view of a BF detector 120, ADF detector 121, and HAADF scintillator surface 130 are shown. Electrons 116 and 118 illustrate different electrons that are scattered from the sample at different scattering angles $\theta_1$ and $\theta_2$, respectively. The signal generated by these electrons is detected by the PMT 150. Since a photon generated from any location on the scintillating surface 134 is transferred to the PMT 150 by the light guide 144, only intensity information is obtained. That is, for every scan pixel of the beam in STEM mode, one pixel data is obtained from the PMT, indicating total intensity from the scintillator. However the spatial information comprising the electron impingement location on the scintillator is lost. Thus, some of the sample material associated information is lost as well.

Moreover, in order to obtain better scattering angle resolution, the optics or the position of the detector needs to be adjusted. For example, the system can be set to be sensitive to a specific angle beforehand, and a scan is then performed. Then the system setup is thereafter changed to be sensitive to another angle, and another scan is performed. In this manner, information relating to specifically selected scattering angles can be obtained and correlated to the atomic composition of the sample. However, it should be appreciated that: i. the specific angle for each scan must be selected beforehand, and ii. a registration procedure must be performed to align the signals from all of the scans. This procedure is tedious, slows the analysis, and may miss important information if the wrong angles are selected. Moreover, some samples get destroyed by the electron beam, enabling only a single scan. To perform a scan for a different angle, another sample must be prepared.

It has also been proposed to use a circular area detector to obtain BF, ADF, and HAADF images simultaneously. The area detector is formed by 16 detectors, each lined via a fiber cable to its dedicated PMT. The signals from the PMT are digitized and displayed on a computer monitor. This arrangement basically replaces the standard, three detectors, BF, ADF and HAADF, arrangement.

In view of the above, a STEM arrangement that enables resolution of the scattering angles without the need for repeated imaging and registration would be beneficial. A STEM arrangement that enables selection of scattering angles after the scan would also be beneficial. Furthermore, a STEM arrangement that enables resolution at several scattering angles simultaneously and using only a single scan would also be beneficial. Furthermore, a STEM arrangement that enables resolution of the scattering angles without disrupting the standard BF detector would also be beneficial.

SUMMARY

The following summary of the invention is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below According to aspects of the invention, STEM systems and methods are provided, which enable discrimination and resolution of the electron scattering angles from the sample without the need for repeated imaging and registration. According to other aspects of the invention, a STEM arrangement is provided that enables selection of scattering angles after the scan has been performed. According to further aspects of the invention, a STEM arrangement is provided that enables resolution of multiple scattering angles simultaneously using only a single scan.

According to various disclosed embodiments, a STEM system is disclosed wherein an imaging system is used to image the plane of the HAADF detector onto a two-dimensional array detector. A data acquisition system conditions and stores the data from the two-dimensional array detector. For each illumination pixel of the STEM, one frame of PMT data is generated and stored. Each PMT frame includes data of all scattered angles and can be analyzed at any time after the scan. Since two-dimensional frame data is stored for each illumination pixel, the user can select data for any arbitrary scatter angle or for multiple angles—even after the scan is completed. Furthermore, the user's selection is not limited to annular angles. For example, the user may select a quadrant or a slice of the HAADF detector—which is not possible with any prior art STEM. Thus, in addition to providing more data, the disclosed system allows more flexibility than the prior art systems.

Various embodiments may be used to image the scintillator plane of the HAADF detector. For example, the HAADF detector may have a scintillating surface emitting photons upon detection of electrons. The scintillating surface is then optically imaged onto a two dimensional array detector, such as a multi-wire or multiple-anode photomultiplier tube (PMT), a multi pixel Si-PM array, or a multi anode MCP-PMT device. For each pixel of the STEM scan, the data acquisition system conditions and stores a frame from the multiple-anode PMT. As can be understood, the stored data includes data for all measured scattered angles, with intensity and spatial resolution on the scintillator surface.

By registering the electron impingement location it is possible to re-construct a sample image from electrons that are scattered at any selected angle. With such a system, the operator is able to simultaneously define few groups of electrons (electrons with different scatter directions) and generate simultaneously independent sample images by each pre-defined group and, in addition, discriminate against events in which more than one electron at a time are detected. This may lead to better identification of the sample atomic composition. Additionally, the proposed detection system is capable of detecting very low signals such as electron current on the detector in the range of 1-1000 Femto-Ampere.

Embodiments disclosed herein provide a HAADF detector assembly operating within a STEM, provided to detect electrons emitted from a sample, being scanned by an electron beam, and comprising a scintillating surface for emitting light signals due to impingement of scattered electrons thereon; a two-dimensional sensor having a light sensing surface (e.g. a sensor having n×k sensor elements); an optical imaging system imaging the scintillating surface onto the light sensing surface of the two-dimensional sensor by transferring light signals produced in a specific location of the scintillating surface onto a corresponding position on the light sensing surface and thereby maintaining spatial information of the light signals; and, an image processing unit receiving output signal from the two-dimensional sensor and providing information of images related to selected positions of the electrons impinging the scintillation surface.

According to other aspects, a HAADF detector assembly operating within a STEM is provided, comprising: a sensing surface for sensing scattered electrons passing through a sample; a sampling unit coupled to the sensing surface and generating a plurality of signals indicating amplitude and spatial location of impinging electrons on the sensing surface; and, an image processing unit simultaneously generating a plurality of video signals, each corresponding to a selected group from the plurality of signals. In some embodiments the sensing surface is configured to output an optical signal corresponding to each sensed electron, and wherein the sampling unit is configured for detecting the optical signal and output a corresponding electrical signal.

A method is disclosed for detecting electrons emitted from a sample by detecting electrons scattered from the sample and generating plurality of corresponding signals, each signal indicative of scattering angle of a scattered electron; generating a plurality of signal groups, each signal group being a collection of signals of a user selected scattering angle; and converting each of the signal groups into an individual video signal and displaying the video signal on a monitor.

According to some aspects, a HAADF detector assembly operating within a STEM is provided to detect electrons emitted from a sample that is being scanned by an electron beam, including a scintillator including an annular scintillating plate having a scintillating surface and a central aperture configured to enable passage of non-scattered electrons, the scintillating surface emitting light signals corresponding to impingement of scattered electrons thereupon, a two-dimensional sensor having a light sensing surface and plurality of electrical outputs, an optical imaging system configured to form an image of the scintillating surface on the light sensing surface of the two-dimensional sensor by transferring light signals produced in any specific location of the scintillating surface onto a corresponding position on the light sensing surface and thereby maintaining spatial information of the light signals, and, an image processing unit receiving output signals from a plurality of electrical outputs of the two-dimensional sensor and providing information of images related to selected positions of the electrons impinging the scintillation surface.

The optical imaging system may include a mirror having an aperture configured for passing non-scattered electrons. The detector assembly may further include a lens positioned between the mirror and the two-dimensional sensor. The detector assembly may further include a second lens positioned between the mirror and the scintillator, the second lens having an aperture configured for passing non-scattered electrons. The two-dimensional sensor may include one of a multi-wire photomultiplier tube or multi-anode photomultiplier tube or multi anode MCP-PMT.

The optical imaging system may include a coherent fiber optic bundle. The two-dimensional sensor may include n by k sensor elements, and wherein the image processing unit is configured to sample a frame of n×k pixels for each one pixel of the electron beam scan. The image processing unit may include n×k pre-amplifiers, each coupled to a corresponding one of the n×k sensor elements. The image processing units may include N simultaneous outputs, each programmable to provide an output signal corresponding to a group of selected sensor elements. Each of the group of selected sensor elements may define an annular ring or a section of an annular ring. The optical imaging system may further include a variable magnification lens assembly.

According to some aspects, a HAADF detector assembly operating within a STEM is provided, including an annular electron sensor having a sensing surface configured for sensing scattered electrons passing through a sample and having a central aperture configured to pass non-scattered electrons, a sampling unit coupled to the sensing surface and generating a plurality of signals indicating amplitude and spatial location of impinging electrons on the sensing surface, and, an image processing unit simultaneously generating a plurality of video signals, each corresponding to a selected group from the plurality of the sensor signals.

The sampling unit may include a two-dimensional light sensor array. The plurality of video signals may correspond to a selected scattering angle range of the scattered electrons or selected area on the annular electron sensor. The detector assembly may further include a variable magnification lens arrangement.

According to some aspects, a method for detecting electrons emitted from a sample in a scanning transmission electron microscope is provided including using a scintillating plate for detecting electrons scattered from the sample, projecting an image of the scintillating plate onto a two-dimensional light sensor and generating plurality of corresponding signals, each signal indicative of scattering angle of a scattered electron, generating a plurality of signal groups, each signal group being a collection of signals of a user selected scattering angle range, converting each of the signal groups into an individual video signal and displaying the video signal on a monitor.

The method may further include allowing non-scattered electrons to pass through an aperture in the scintillating plate. The method may further include storing the corresponding signals in a computer memory to enable post processing. The method may further include recording all detected sensor signal for off-line selection and evaluation of various regions of interest. Projecting an image may further include varying the magnification of the projected image.

These and other aspects of the present invention will become apparent to those skilled in the art after a reading of the following description of various embodiments when considered with the drawings.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIGS. 1A&1B are a simplified sectional illustration of a conventional TEM/STEM system and a simplified sectional illustration taken along lines IB-IB in FIG. 1A;

FIGS. 9A and 9B are simplified illustrations of two-dimensional sensors, wherein FIG. 9A is related to the multi wire position sensitive PMT configuration, while FIG. 9B is related to the multi anode PMT configuration.

DETAILED DESCRIPTION

In the following description, various aspects of the present invention will be described with reference to different embodiments. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

As eluded to in the Summary section, various embodiments which will be described below provide an improved STEM system, which may be a stand alone or an add-on to a standard TEM system. As shown in the embodiments disclosed below, an optical imaging system is used to image the plane of the HAADF detector onto a two-dimensional array detector. This arrangement preserves the spatial information of the exact location where the electrons hit the HAADF detector. Consequently, at each pixel location of the electron beam scan, data is generated for electrons at all scattering angles simultaneously. The saved data can be manipulated to highlight any desired angle or sector of the HAADF detector. Moreover, the operation of the existing BF detector is not disrupted.

Figure 2:
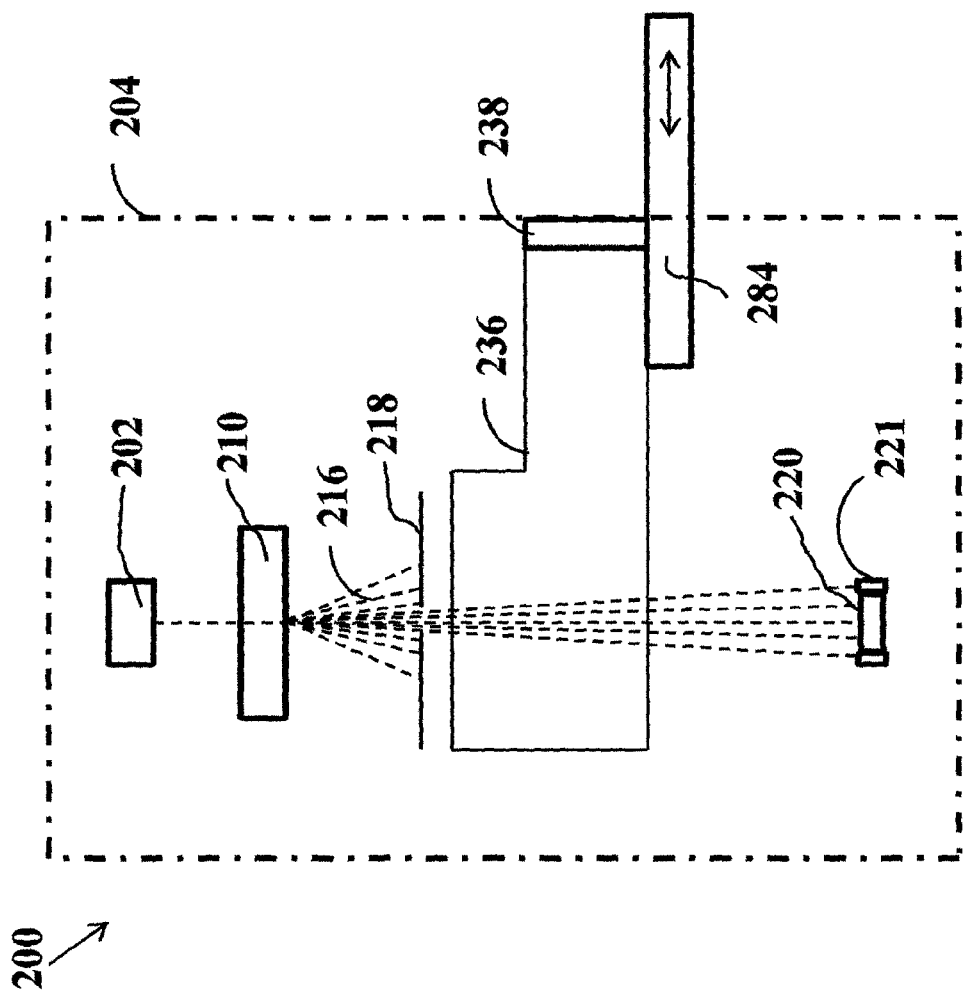
FIG. 2 is a simplified schematic illustration of major parts of a TEM/STEM system according to an embodiment of the invention.

FIG. 2 is a simplified schematic illustration of major parts of a TEM/STEM system according to an embodiment of the invention. Elements in FIG. 2 that are similar to those illustrated in FIG. 1A are referenced by the same reference numerals, except that they are in the 2xx series. For example, all of the elements relating to operation in TEM mode can remain the same as in the prior art. However, some of the elements relating to STEM operation are changed. FIG. 2 illustrates the system in a position for performing STEM operation.

In FIG. 2, electron source 202 provides a beam of electrons, which, for STEM mode of operation, is demagnified by one or more lenses, e.g., electrostatic lenses (not shown), to be focused onto a point on the sample 210. The beam is then scanned over a desired area of the sample 210, wherein each scanned point can be considered an illumination pixel or scan pixel. Some of the electrons pass directly through the sample 210 and are detected by bright field detector 220, some are deflected by a small angle and are detected by dark field detector 221, and some are deflected by larger angles and are detected by HAADF detector 218. HAADF detector 218 is an annular detector with a center aperture allowing electrons to pass to the bright field and dark field detectors 220 and 221, respectively. In FIG. 2, the detection surface of HAADF detector 218 is illustrated. For example, when HAADF detector 218 is a scintillator, FIG. 2 references the scintillating surface of the scintillator.

An imaging optics 236, which may include light optics such as, e.g., lenses, mirrors, etc., is used to image the detection surface of HAADF detector 218 onto a two-dimensional array detector 238. The two-dimensional array detector 238 may reside inside or outside the vacuum enclosure 204. When HAADF detector 218 is a scintillator, the scintillating surface is imaged by imaging optics 236 onto detector 238. Since the detecting surface of HAADF detector 218 is imaged onto two-dimensional detector 238, spatial information of electrons hitting the HAADF detector 218 is transferred onto the two-dimensional detector 236. In that respect, the imaging optics 236 onto detector 238 can be considered to form a sampling unit which is coupled to the sensing surface and generating a plurality of signals indicating amplitude and spatial location of impinging electrons on the sensing surface. However, unlike prior art systems which generate one sample pixel for every one scanned pixel, in the embodiment of FIG. 2, one frame of sample pixels are generated and stored for each scan pixel. To illustrate, if HAADF detector 218 is a two-dimensional array of 16×16 pixels, it provides 256 pixels for each one illumination pixel. For example, when the STEM system illuminates the sample at a rate of 100K pixels/second, the data rate of HAADF detector 218 is 25.6 M pixels/second.

Specific examples for implementing the imaging optics 236 and two-dimensional array detector 238 will now be described, but it should be appreciated that other means for achieving the imaging may also be used. Each of FIGS. 3A-3D, illustrates a simplified schematic of a TEM/STEM system 300 constructed and operative in accordance with an embodiment of the present invention, while FIGS. 4A-4C, illustrate simplified schematics of optional optical imaging systems that can be incorporated in TEM/STEM systems. Similar items are identified with same reference numerals, but may be in a different centennial series. In each of FIGS. 3A-3D, the TEM/STEM system 300 comprises an electron beam column 302 within a vacuum chamber 304. The electron beam column 302 emits an electron beam 306 which is focused for scanning a sample 310 during the scanning mode of the TEM/STEM system 300. Electrons 314 are scattered by the sample 310 following impingement of the electron beam 306 thereon. The un-scattered electron beam 306 that passes through the sample may be detected by a standard Bright Field detector 320.

In accordance with an embodiment of the invention, the TEM/STEM system 300 may comprise an Annular Dark Field detector assembly 324 that can be used also as a High Angle Annular Dark Field detector, comprising a two dimensional sensor assembly 326, which may include, for example, a multi-wire anode PMT array, a multi-anode PMT, multi anode MCP-PMT, etc. The two dimensional sensor assembly 326 is provided to detect a scattered electron signal and the spatial location of the scattered electron according to the spatial location of the input signal impinging upon a scintillator, as described herein. The angular scattering distribution function of the STEM beam electrons depends on inter alia: the electron beam energy, sample 310 material structure, type of interacting atom in the sample (Z number) and sample thickness. The capability to measure the scattered atom distribution may lead to improved re-construction of the atomic structure of the sample 310.

Figure 9A:
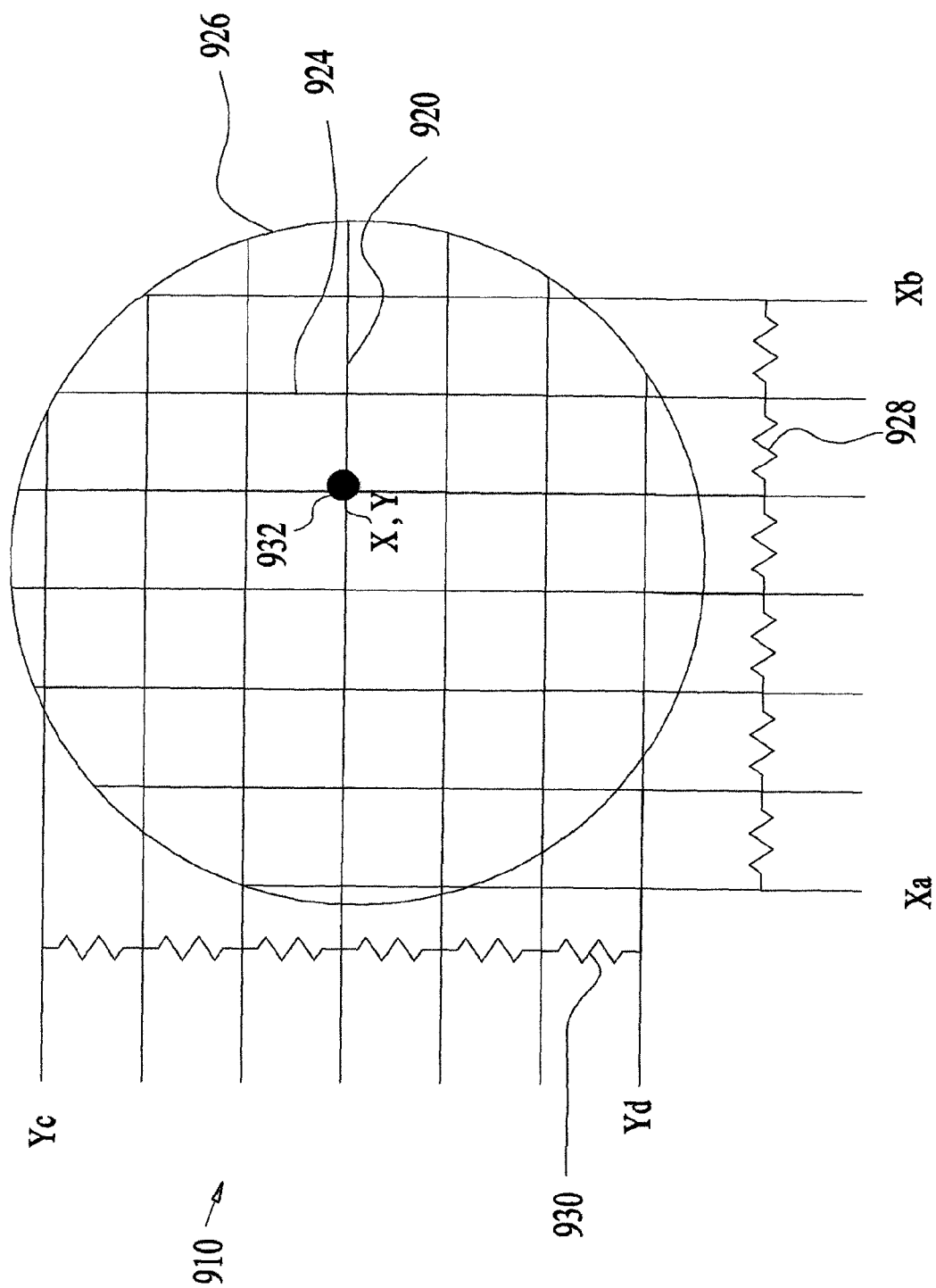
Figure 9B:
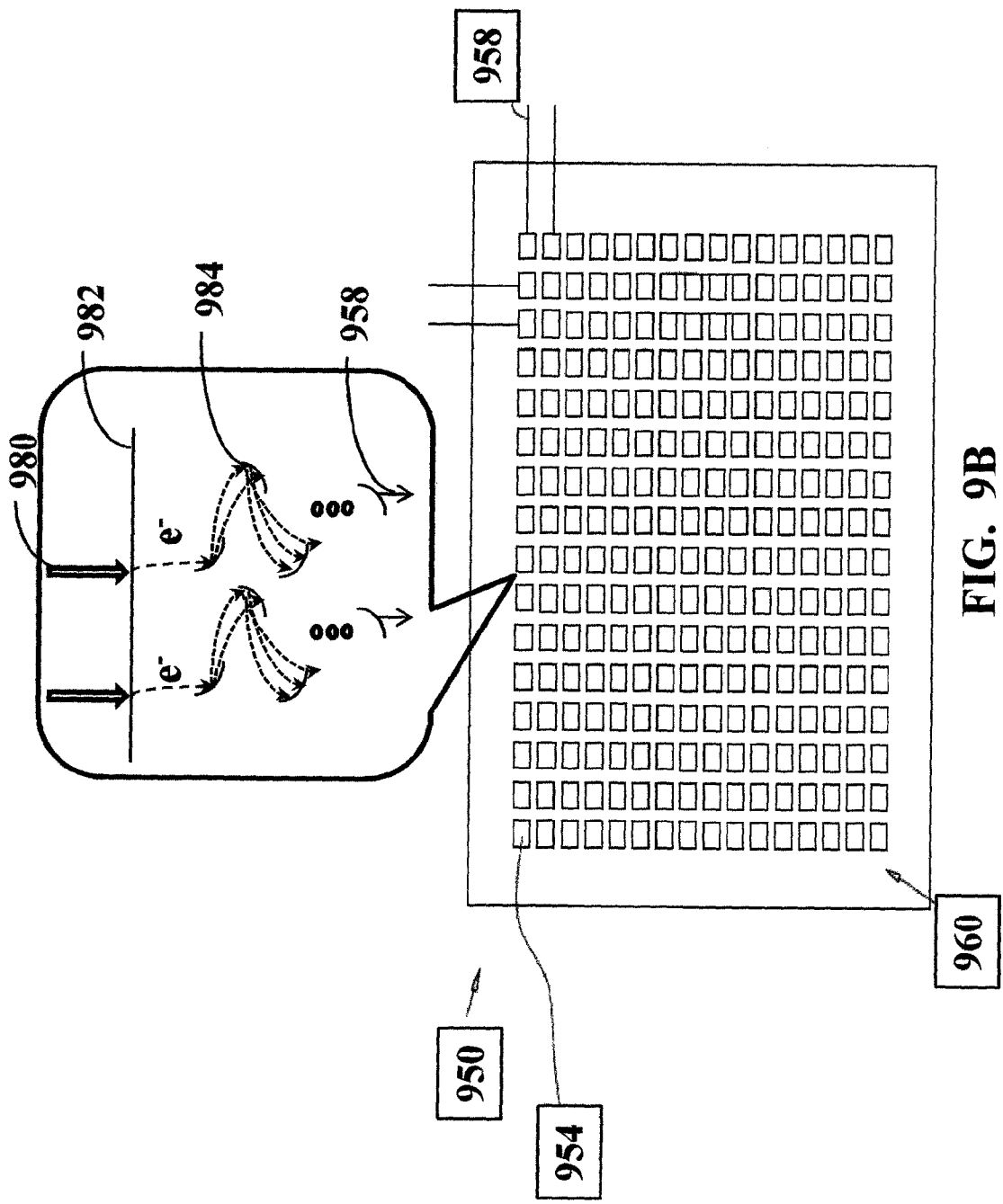

The two dimensional sensor can be formed as a position sensitive PMT having a plurality of electron multiplying elements. When a photon impinges upon the photocathode of the position sensitive PMT, it starts a multiplication chain and induces a swarm of electrons that reach an anode plane at a corresponding location as illustrated in FIG. 9B. The position sensitive PMT may also comprise a multi-wire anode array, such as that commercially available from Hamamatsu under catalogue No. R2486 or R3292. It is recognized that the invention can be implemented with a position sensitive PMT based on signals obtained from corners of a resistive anode, or from anodes formed by delay lines, as well. In additional embodiments the position sensitive PMT may comprise a multi anode array, such as that commercially available from Hamamatsu under catalogue No. R8900 or H9500, or a multi anode MCP-PMT catalogue No. XP85022 from Photonis. A multi anode array may feed into independent channels that measure the output readout of each anode wire. Another embodiment can include a multi pixel array of silicon photomultiplier (Si-PM).

In accordance with an embodiment of the invention, an electron 314 may impinge upon a scintillating surface 334, which may be formed with an aperture 340 for allowing the unscattered electrons to pass through to the Bright Field detector 320. The scintillating surface 334 may be configured in any suitable manner, such as with an annular surface area, similar to the surface area of the scintillator based detector assembly 130 shown in FIG. 1B. Upon impingement of an electron 314 on the scintillating surface 334, a light signal 342 is formed and imaged onto the two-dimensional sensor assembly 326. The light signal 342 may be imaged onto the two-dimensional sensor assembly 326 in any suitable manner, such as by utilizing any optical imaging system. The main objective of the imaging system is to collect as much light as possible from the scintillator and transfer it efficiently to the two-dimensional sensor assembly 326, preserving the spatial position of the light emitted by the scintillator.

Examples of optical imaging systems are shown in FIGS. 4A-4C.

Figure 3A:
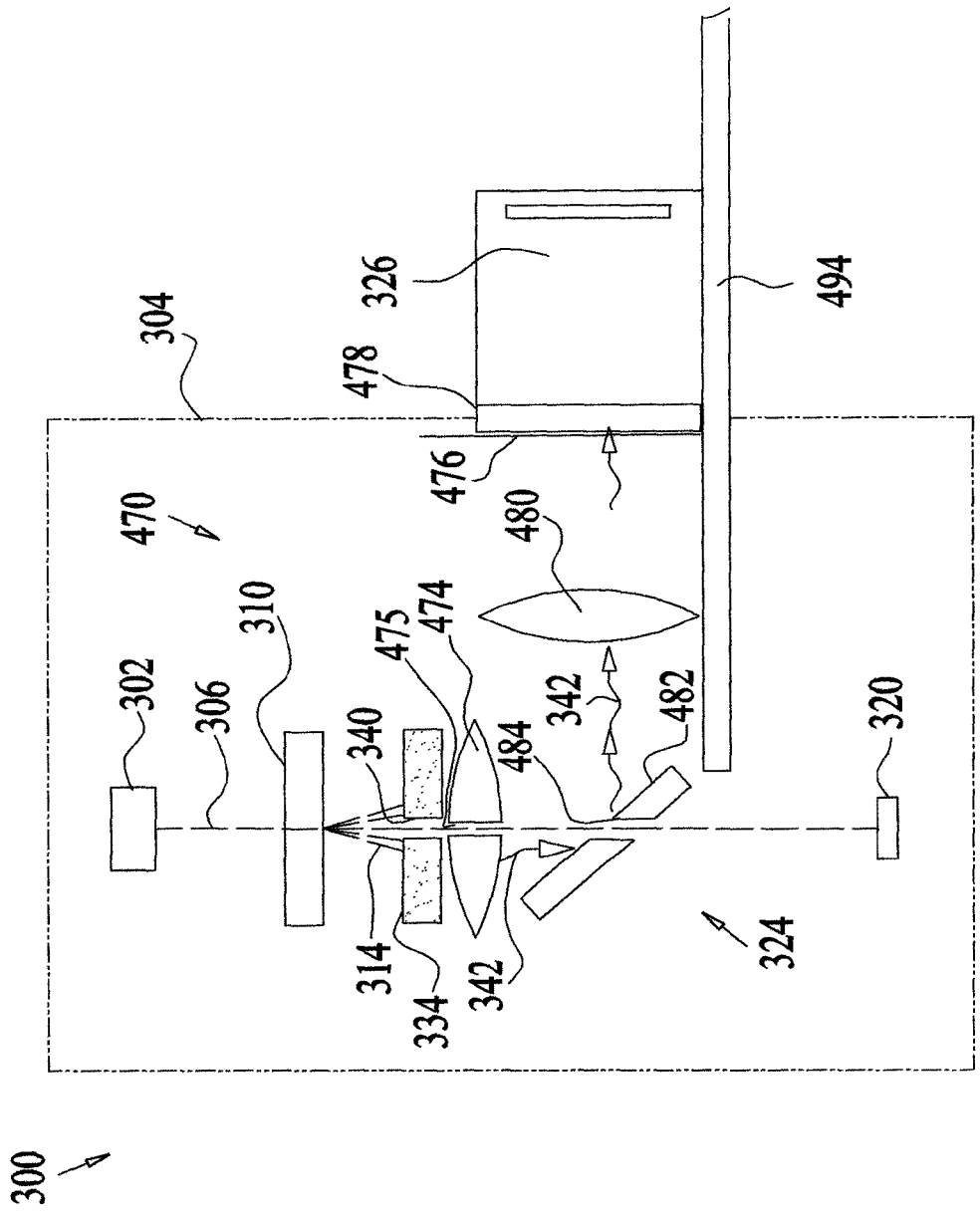
FIGS. 3A-3D are each a simplified sectional illustration of a TEM/STEM system constructed and operative in accordance with embodiments of the present invention.
Figure 4A:
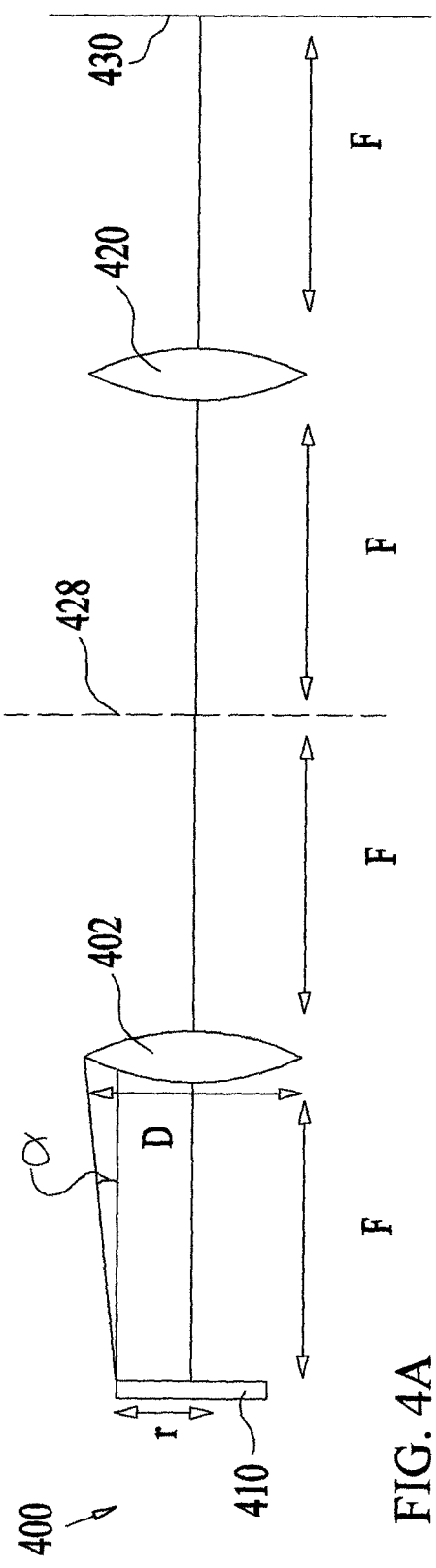
FIGS. 4A-4C are each a simplified schematic illustration of an optical imaging system for a TEM/STEM system constructed and operative in accordance with embodiments of the present invention.
Figure 4B:
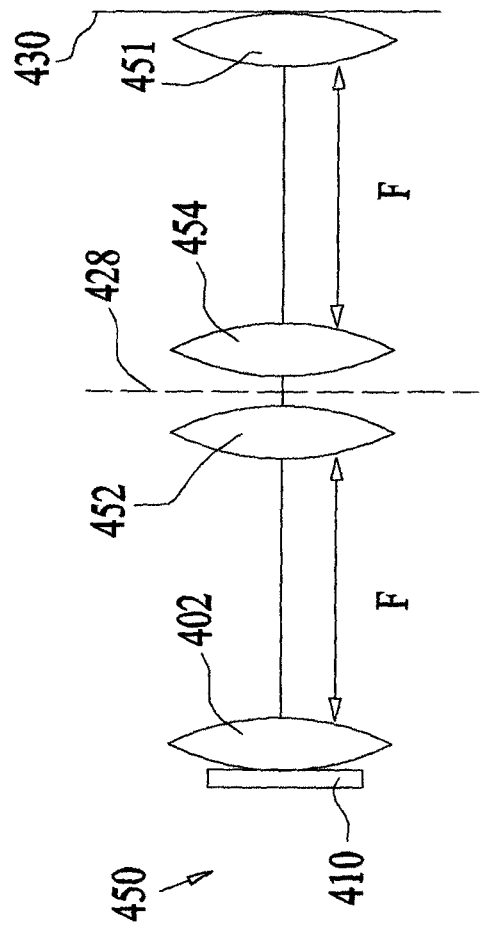
Figure 4C:
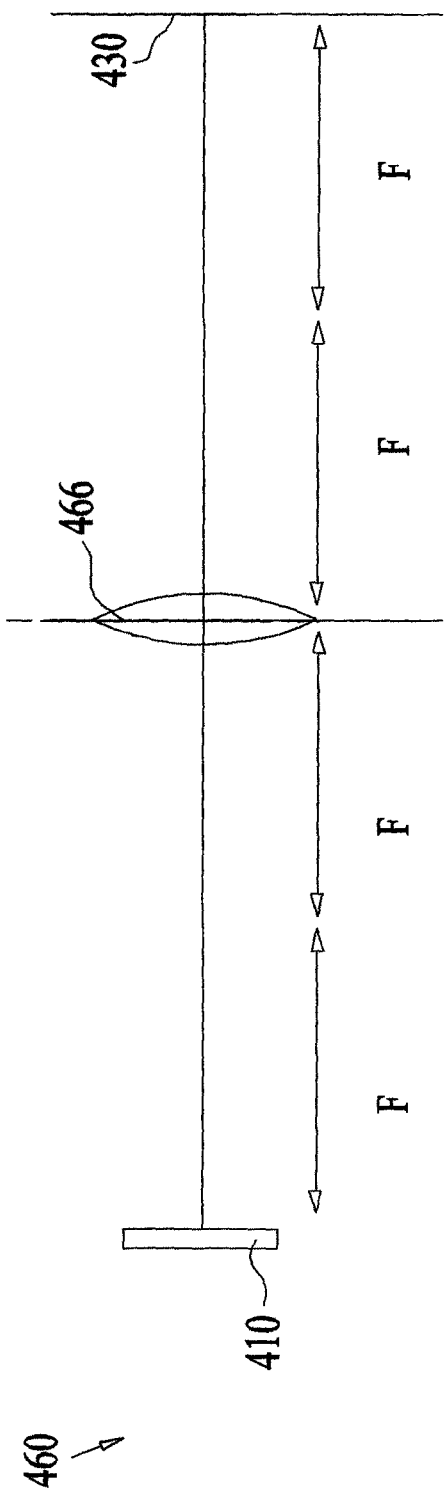

Turning to FIG. 4A, a 4F imaging system 400 is illustrated, corresponding to the embodiment of FIG. 3A. A first lens 402 collects light emitted from an object 410 with a radius r. The first lens 402 is positioned at a distance "F" from the object 410, where F is the focal length of the lens 402. A second lens 420 is placed at a distance "2F" from lens 402. The image of the object 410 is obtained at an image plane 430 which is at a distance F from lens 420. Plane 428 which is placed at a distance F from lenses 402 and 420 is known in the art as a Fourier plane. As seen in FIG. 4A, the distance between an image plane 430 and the object 410 is 4F.

The amount of light collected from the object is determined by the numerical aperture (NA) of the imaging system. For a light ray to be emitted with an angle $\alpha$ from the object and imaged onto the two-dimensional sensor, the diameter D of lens 402 should fulfill the condition: $D > 2 (r + l \tan \alpha)$. Wherein r represents the object radius and l represents the distance between the object 410 and the first lens 402. It is evident that the greater the distance l between the object 410 and the first lens 402 and the greater the collection angle $\alpha$, a larger diameter D is required.

Turning to FIG. 4B a "2F" imaging system 450 is illustrated. The first lens 402 is proximal to the object 410. A second lens 452 is placed at a distance F from lens 402. The lens couple 402 and 452 performs a Fourier transform of the object 410. The distance between the object 410 and its Fourier plane 428 is F. The inverse Fourier transform of the image is performed by the pair of lenses 454 and 451. Thus the distance between the object 410 and the image plane 430 is reduced to 2F. Additionally, as the object 410 is positioned in proximity to the first lens 402, the distance l between the object 410 and the first lens 402 is very small and thus the diameter of the first lens 402 may accordingly be relatively small with relatively high light collection efficiency from the object 410. In practice lenses 452 and 454 can be combined into one lens, as seen for example in FIG. 3B, wherein lens 480 functions as the combination of lenses 452 and 454.

In FIG. 4C an alternative "4F" imaging system 460 is illustrated. A lens 466 is provided at a 2F distance from the object 410 and at a 2F distance from the image plane 430. The object 410 is imaged by lens 466 at image plane 430. As seen in FIG. 4C, the distance between the image plane 430 and the object 410 is 4F.

The optical configurations described with the aid of FIGS. 4A-4C illustrate imaging concepts with unity magnification. By changing the lens focal length and position it is possible to achieve a magnification different from unity, thereby forming variable magnification. For example, in FIG. 4A, the focal length F of lens 402 is equal to the focal length F of lens 420. On the other hand, if lens 420 is replaced by a lens having focal length of 2F, then the magnification would be double. Similarly, in FIG. 4B, if the focal length F of lenses 454 and 451 is changed, the magnification would be changed accordingly. This change of magnification can be achieved by, for example, using a turret having multiple lenses. Alternatively, an optical zoom lens system can be employed to provide continuously variable optical magnification.

Figure 3B:
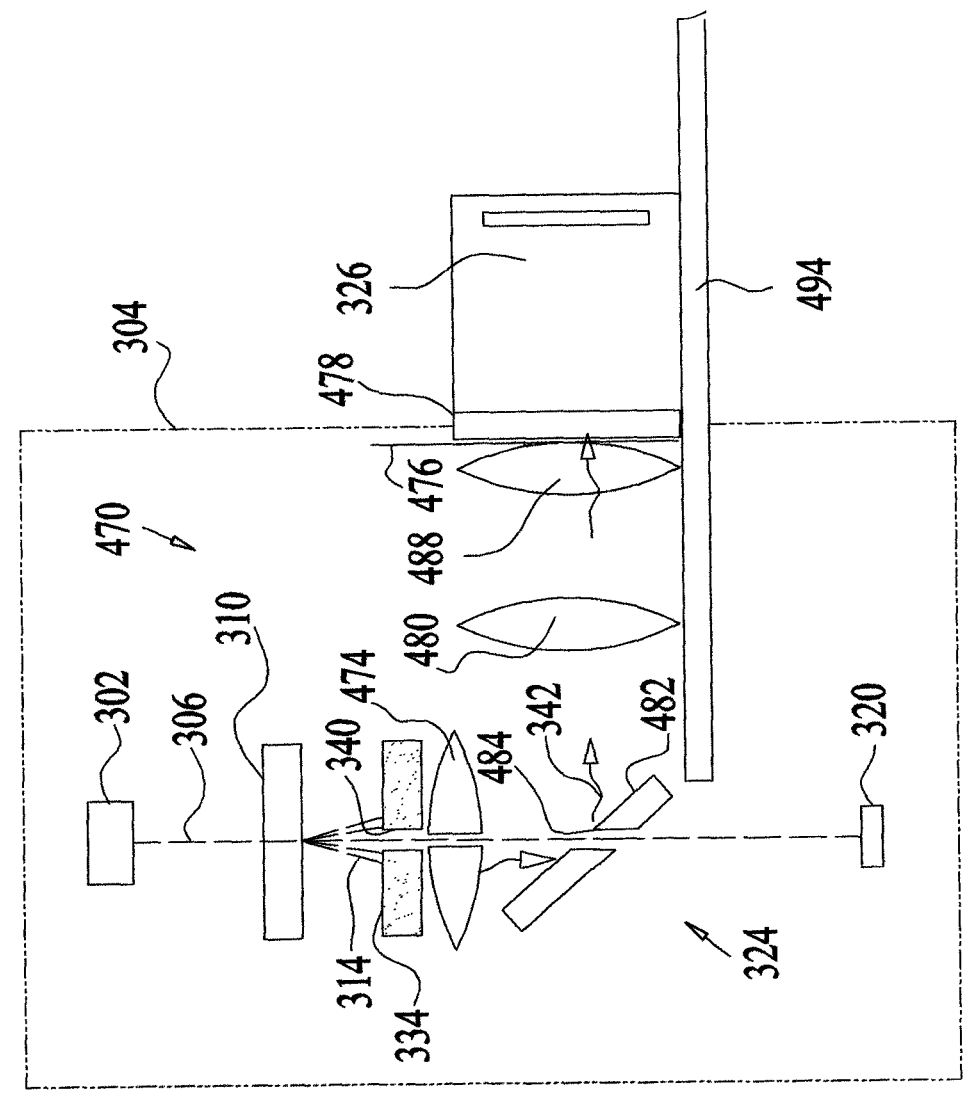

As seen in FIG. 3A, a 2F imaging system 470 similar to that illustrated in FIG. 4B, may be introduced so as to provide an image of the light signal 342 from scintillating surface 334 onto the two-dimensional sensor assembly 326. A first lens 474 may be placed in proximity to the scintillating surface 334. The first lens, 474 operating as lens 402 (FIG. 4B), may be formed with an aperture 475 for allowing the un-scattered electrons to pass through to the Bright Field detector 320. A magnified image is obtained at an image plane 476 at the entrance to the two-dimensional sensor assembly 326. The two-dimensional sensor assembly 326 can be placed outside the vacuum chamber 304. The light may pass through a window 478. A lens 480 operating as the pair of lenses 452 and 454 (FIG. 4B) is positioned intermediate the scintillating surface 334 and the two-dimensional sensor assembly 326 at a distance "F" from the scintillating surface 334 and a distance "F" from the two-dimensional sensor assembly 326. The light signal 342 is directed from the first lens 474 to the second lens 480 by a mirror 482. Mirror 482 may be formed with an aperture 484 for allowing the electrons to pass through to the Bright Field detector 320. The mirror 482 may be configured in any suitable manner, such as with an annular surface area. An additional lens 488 operating as lens 451 in FIG. 4B may be provided, as shown in FIG. 3B.

Utilizing the optical imaging system 470 in the TEM/STEM system 300 is advantageous since the optical imaging system 470 does not occupy a large space within the relatively crowded vacuum chamber 304. Additionally, the optical imaging system 470 provides for maximal collection of light signals emitted from the scintillating surface 334, which can be positioned at an angle normal to the electron beam direction. This is due to the substantial proximity of the first lens 474 to the scintillating surface 334.

Figure 3C:
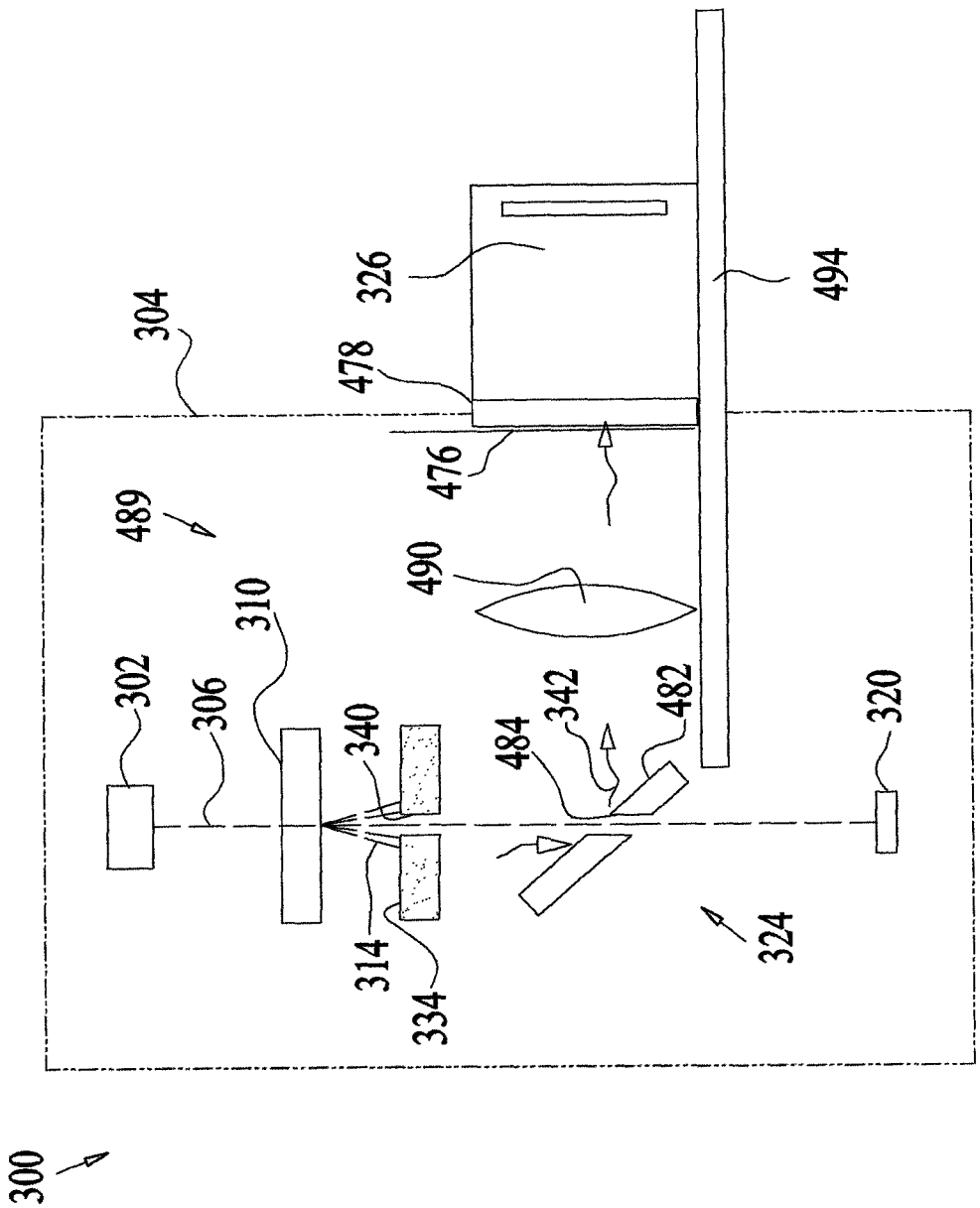

It is noted that the 4F optical imaging system 400 of FIG. 4A may replace the 2F optical imaging system 470. Additionally, the 4F optical imaging system 460 of FIG. 4C may replace the 2F optical imaging system 470, as seen in FIG. 3C. In FIG. 3C an optical imaging system 489 comprising a lens 490 may be placed at a distance 2F from the scintillating surface 334 and at a distance 2F from the image plane 476. The embodiment of FIG. 3C is advantageous as lens 490 is outside the optical axis of the electron beam and need not have an aperture for passing electrons to the bright field detector.

Thus it is seen that in accordance with an embodiment of the invention a TEM/STEM system comprises an optical imaging system for imaging a light signal to be detected by a two-dimensional sensor. Also, in accordance with an embodiment of the invention a method is provided for imaging the geometrical location of the electrons 314 impinging the annular scintillator surface onto a corresponding location on the two-dimensional sensor 326. That is, the surface of the annular detector is imaged onto the detection plane of a two-dimensional sensor 326.

Figure 3D:
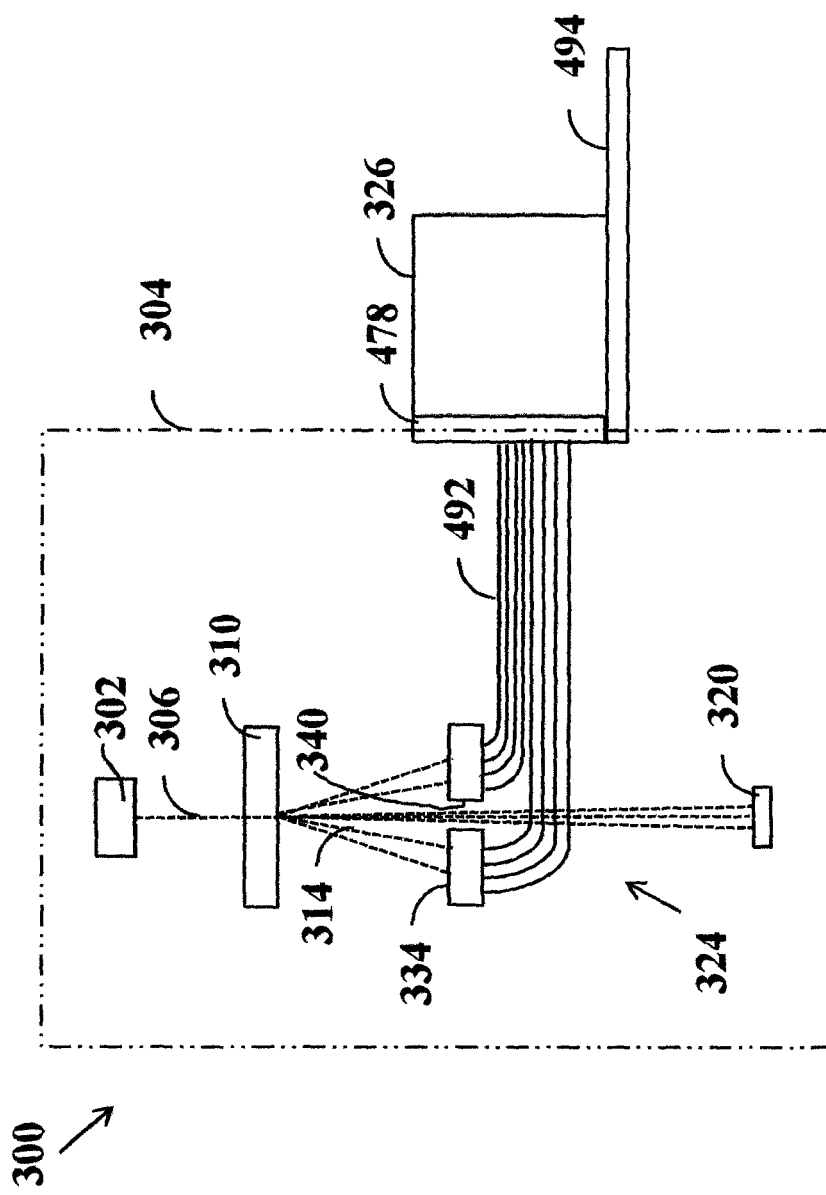

In the embodiments of FIGS. 3A-3C, the scintillating surface 334 is positioned orthogonally to the optical axis of the electron beam 306. An annular mirror 482 and optical imaging system 470 of FIGS. 3A and 3B or optical imaging system 489 of FIG. 3C collect the light from the scintillator and image it onto the surface of the sensor 326, which, in the embodiments of FIGS. 3A-3C, is placed orthogonally to the scintillator. However, other imaging system may be used, which do not use mirrors and/or lenses. For example, the embodiment of FIG. 3D illustrates an imaging system that does not use mirror or lenses. As seen in FIG. 3D, an array or bundle of optical fibers 492, such as a coherent bundle of optical fibers, may be utilized for directing light signals to the two-dimensional sensor assembly 326. The optical fibers 492 may replace the optical imaging system 470 of FIGS. 3A and 3B or optical imaging system 489 of FIG. 3C. More specifically, a HAADF detector has an annular scintillating surface 334, having an aperture 340 in the center to enable electrons to reach the BF detector 320. The coherent bundle of optical fibers 492 is arranged to collect light from the back surface of the scintillating surface 334, without obscuring the path of the electrons to the BF detector. The coherent bundle of optical fibers 492 maintains spatial information of the light from the scintillating surface, and delivers the light to two-dimensional sensor assembly 326, while maintaining the spatial information.

The elements of the STEM system of any of the described embodiments may be engaged with a retracting mechanism 494. The retracting mechanism 494 is provided to dislodge the position of the scintillator, the two-dimensional sensor assembly 326 and imaging system 470 of FIGS. 3A and 3B, imaging system 489 of FIG. 3C or optical fibers 492 of FIG. 3D, from the path of the electron beam in order to enable the TEM mode operation.

The signal collected from the two-dimensional sensor assembly 326 is processed in a data acquisition system. A data acquisition system associated with a multi-wire anode array of the two-dimensional sensor assembly 326 is described in reference to FIGS. 5-7. A data acquisition system associated with a multi-anode array of the two-dimensional sensor assembly 326 is described in reference to FIG. 8. Examples of two-dimensional sensors are illustrated in FIGS. 9A and 9B. FIG. 9A illustrates a multi-wire anode array, while FIG. 9B illustrates a multi-anode array. Such sensors are generally referred to herein as position sensitive PMT.

As seen in FIG. 9A, a multi wire anode array 910 comprises a plurality of spaced apart horizontally oriented anodes 920 overlying and generally not touching a plurality of spaced apart vertically oriented anodes 924. Anodes 920 and anodes 924 are placed within the vacuum 926 of the position sensitive PMT assembly. The anode wires extend by pins through the vacuum case of the photomultiplier tube. A way of determining the position of the signal is to connect a resistor chain 928 outside the vacuum between horizontally adjacent oriented anodes 920. The vertically oriented adjacent anodes pins 924 are formed with another resistor chain 930 at an end thereof. The position of the signal is derived from the output signals obtained at Xa, Xb, Yc, and Yd.

For example, the horizontal coordinate X of an input signal 932 is derived by calculating the voltage measured at Xa relative to the total voltage Xa+Xb, and represented by Xa/(Xa+Xb). Similarly, the vertical coordinate Y of the input signal 932 is derived by calculating the voltage measured at Yc relative to the total voltage Yc+Yd, and represented by Yc/(Yc+Yd). It is important to note that this configuration is suitable only for pulse counting. In pulse counting the location is determined for one impinging electron at a time interval. The time interval is the time needed to determine the location of the impinging electron and reset the measuring electronics to await the next electron. Turning to FIG. 9B, the anode layout of a multi anode based position sensitive PMT 950 is shown. As illustrated in the callout for two pixels, as photons 980 impinge on the photocathode 982, they generate electrons, which are accelerated towards a series of dynodes 984. The series of dynodes causes a multiplication of electrons, generating a signal at the output 958. An analog output signal is extracted independently from each anode 954. The position coordinates of the impinging photons is simply known from the position of the associated readout anode (pixel) via the respective output wire 958. The readout electronics of such a device is similar to that of a CMOS sensor array that is commonly used in commercial digital cameras. The anodes 954 may form a K×K anode array 960. It is noted that although in FIG. 9B only a number of anodes 954 are shown with output wires 958, each anode 954 comprises an output wire 958.

Figure 5:
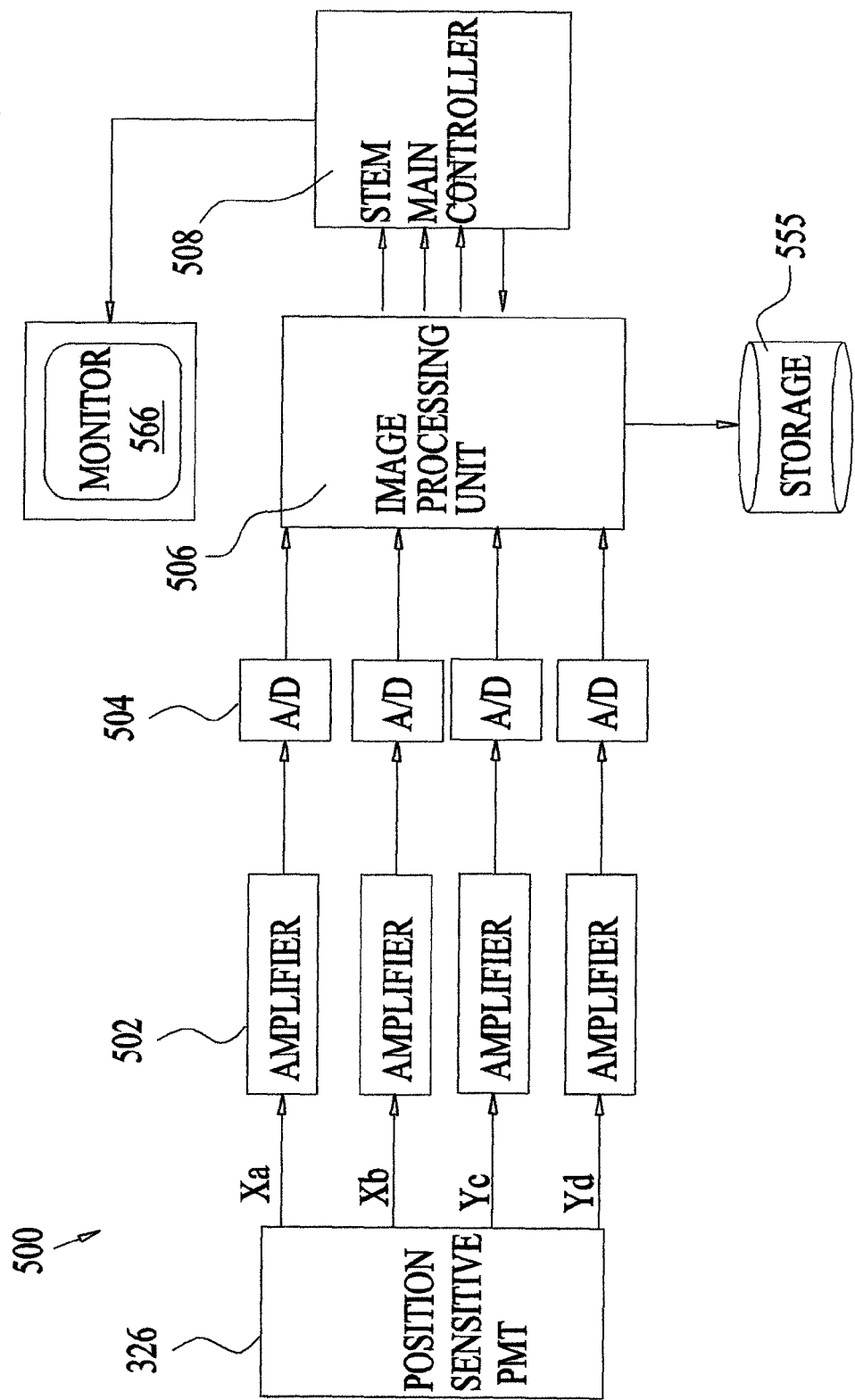
FIG. 5 is a simplified schematic illustration of a general data acquisition system associated with the STEM system of FIGS. 3A-3D.

Turning to FIG. 5, an example of a pulse counting data acquisition system for use with a multi-wire PMT is illustrated. In the data acquisition system 500, the properties Xa, Xb, $Y_c$ and Yd of a signal are each transferred from the position sensitive PMT assembly 326 to an amplifier 502 and then each amplified property is digitized by an Analog to Digital Converter 504. The digital outputs are then fed to an image processing unit 506 that can record the digital values with a digital signature of the STEM electron beam position and may be displayed on monitor 566. The recorded events comprising the digital values of Xa, Xb, Yc, Yd and the pixel location in the STEM are stored sequentially, one after another, in a fast large memory 555 of the image processing unit 506 which is in communication with a STEM main controller 508.

Figure 6:
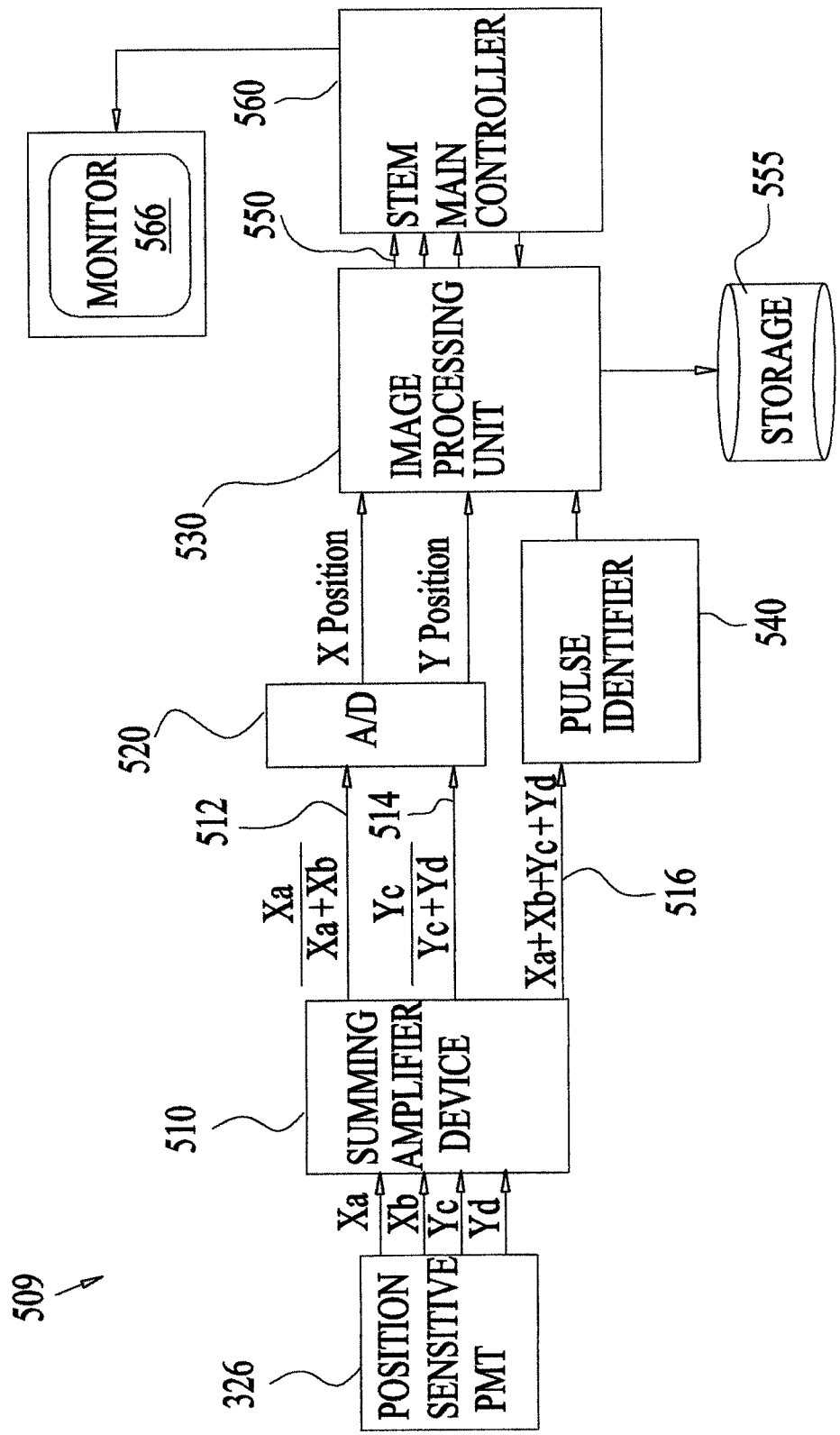
FIG. 6 is a simplified schematic illustration of a more specific data acquisition system associated with the STEM system of FIGS. 3A-3D.

An example of a more specific data acquisition system 509 is illustrated in FIG. 6. In such a system the analog signals $X_a$, $X_b$, $Y_c$ and $Y_d$ from the position sensitive PMT assembly 326 are transferred to a dedicated summing amplifier device 510 that has three outputs: output 512 comprising $X=X_a/(X_a+X_b)$; output 514 comprising $Y=Y_c/(Y_c+Y_d)$; and output 516 comprising $X_a+X_b+Y_c+Y_d$. The first two outputs 512 and 514 calculate the center of mass position of the location of the electron impingement in the X and Y coordinates, respectively. The third output 516 is the total signal measured by the position sensitive PMT assembly 326, i.e. the intensity of the signal. The position signals 512 and 514 are thereafter digitized by an A/D converter 520 and transferred to an image processing unit 530 and may be displayed on monitor 566.

Figure 7:
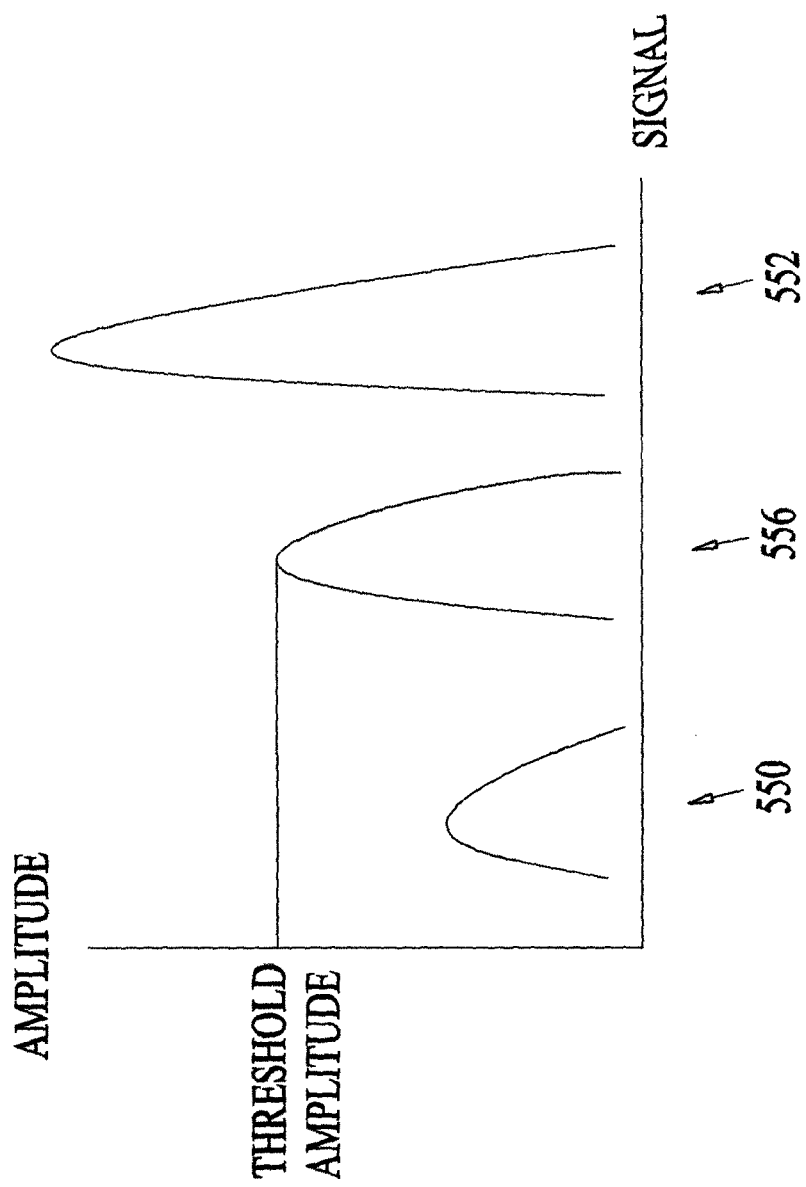
FIG. 7 is a simplified graph of signal filtration with a combination of analog and digital data acquisition systems of FIG. 5 or 6.

The total signal 516 passes through a pulse identifier 540 wherein undesired signals are filtered. As seen in FIG. 7, a desired window for a signal amplitude may be predetermined. A signal 550 with an amplitude lower than the threshold or a signal 552 with an amplitude higher than the threshold will not be transmitted by the pulse identifier 540. A signal 556 within the window limits is transmitted to the image processing unit 530 for immediate processing or for storing in a fast digital storage system for further post processing.

The image processing unit 530 is synchronized with the STEM primary beam scanning, such that for each pixel of the scan, a frame of data is collected from the multi-anode PMT. The gray level of each pixel is proportional to the accumulated number of valid pulses within the integration time of each pixel. The image processing unit 530 can have few video signal outputs 550. Each video signal can be configured by the STEM main controller 560 to generate an image of electrons that impinge a predefined region of interest of the detector and may be displayed on monitor 566. For example, an operator may configure the video signal to originate from electrons that impinge on the scintillator in a radial region of r1<r<r2. In such case, the image processing unit 530 will count the valid pulses wherein the associated coordinated X and Y fulfill the condition: $r_1 < \sqrt{(X^2+Y^2)} < r_2$. The image processing unit 530 counts the valid pulses in time frames that are relatively shorter than the STEM pixel time frame. The number of pulses counted in a pixel time frame is proportional to the signal amplitude of the pixel. The output video signal is originated by converting a pulse-counting signal to a video signal. The image processing unit 530 is operable to simultaneously generate a number of video signals, each representing electron signals that impinge at different areas of the Dark Field detector assembly 326 and correspond to scattering from different types of atoms in the sample 310. For example, the operator may indicate a first signal at $r_1<r_i<r_2$; $r_3<r_j<r_4$; etc.

It is appreciated that any region of interest on the detector assembly 326 may be selected. Additionally, more than one region of interest may be processed and presented simultaneously.

It is noted that the properties $X_a$, $X_b$, $Y_c$ and $Y_d$ of a signal may be processed in any suitable manner to provide any suitable signal or indication of the image of electrons. In accordance with an embodiment of the invention, the video signals representing the electron signals may be stored in any suitable manner. The stored video signals may be retrieved at any desired time, including after secession of imaging by the TEM/STEM system 300. The video signals may be further processed in any suitable manner.

Thus in accordance with an embodiment of the invention there is provided a system and method for detecting the location of the impingement of an electron on the detector thus allowing for imaging a region of interest of the image of electrons.

The data acquisition systems 500 of FIGS. 5 and 509 of FIG. 6 generally operate in a pulse mode and are associated with the position sensitive PMT comprising a multi-wire anode array. That is, in accordance with an embodiment of the invention, a signal measured by the TEM/STEM system 300 is selected to be measured in a pulse mode as apposed to a current mode that is usually used in standard STEM systems. Operating in a pulse counting mode allows detecting relatively low current signals, as low as 1-1000 Femto-Ampere, for example. Operating in the pulse counting mode allows for filtering the noise, since discrete pulses are measured. Operation in a pulse mode is typically applicable with the data acquisition system described in reference to FIGS. 5-7.

Figure 8:
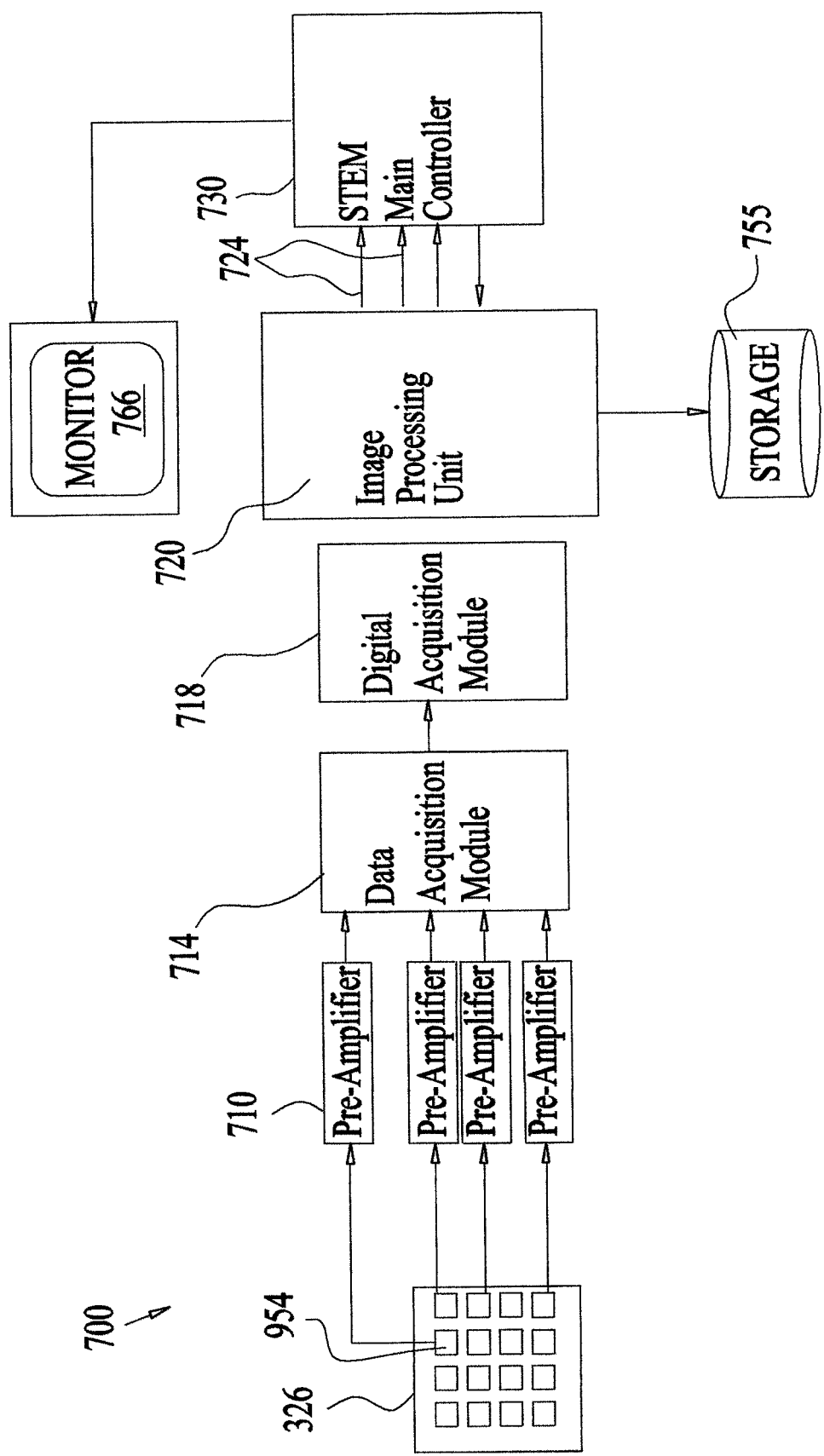
FIG. 8 is a simplified schematic illustration of a data acquisition system associated with the STEM system of FIGS. 3A-3D.

FIG. 8, illustrates a data acquisition system 700 associated with the position sensitive PMT assembly 326 comprising a multi-anode array 950 (FIG. 9B), and generally operating in an analog current mode. It is seen that the output from each anode 954 is individually conditioned by a pre-amplifier module 710. The preamplifiers 710 may be used for gain equalization. That is, as can be appreciated, even if a uniform signal is applied to the entire surface of the multi-anode PMT 326, the signal from the different anodes 954 may not be uniform. Thus, the preamplifier module 710 may be used in a calibration stage to equalize the signal obtained from a uniform illumination, such that the output signal from all of the anodes 954, conditioned by the preamplifier module 710, is of the same magnitude.

The conditioned signal of each channel is then transferred to a data acquisition module 714, that may house another gain/filter stage along with its controllers and the A/D converters. A digital acquisition module 718 combines the signals of all the anodes 954 (pixels) and operates as a digital frame grabber. Such an acquisition module may be implemented using a commercially available module, such as, for example, the module available from Pulse Instruments® under catalogue No. PI-3105. The digital signal from the digital acquisition module 718 is transmitted to the image processing unit 720.

The image processing unit 720 can generate simultaneously N output video signals at the scan rate of the STEM system 300, which may be stored in storage 755 and displayed on monitor 766. In this configuration, the proposed HAADF detector assembly generates the image in the following sequence: The signal generated by the scattered electrons during the one STEM pixel time, is imaged onto the position sensitive PMT assembly 326. The integration time of one frame (K×K pixels) of the position sensitive PMT assembly 326 is equal to one STEM pixel time. Usually, the STEM pixel time is in the range of 1-100 micro-sec. Thus, the entire scatter pattern of each pixel is collected by the multi-anode array of the position sensitive PMT assembly 326 in this pixel time frame. The scatter pattern generated by each STEM pixel time frame is grabbed by the data acquisition module 718 and is transferred digitally to the image processing unit 720.

The image processing unit 720 can generate N video output signal channels 724 simultaneously. The output of each channel is the sum of the defined pixels of the multi anode PMT assembly 326. For example, an operator may configure each video signal to originate from electrons that impinge on the scintillator in a radial region of $rx<r_i<ry$, wherein i=1, 2, 3, etc. In such case, the image processing unit 720 will sum the signal of the multi anode PMT pixels wherein the associated coordinated X and Y fulfill the condition: $r_1<\sqrt{(X^2+Y^2)}<r_2$. However, the region of interest need not necessarily be annular. For example, different quadrants or slices of the detector may also be selected.

The output video signal is originated by converting a sum of the pixels in the region of interest to the amplitude of the video channel. The image processing unit 720 is operable to simultaneously generate a number of video signals 724, each representing electron signals that impinges at different areas of the High Angle Dark Field detector assembly 324 (FIGS. 3A-3B) and corresponds to scattering from different types of atoms in the sample 310. Each video signal can be configured by a STEM main controller 730 to generate an image of electrons that impinge a predefined region of interest of the detector.

In accordance with an embodiment of the invention, simultaneous detection of various types of scattered electrons may be performed by selecting a plurality of regions of the image of electrons to be detected simultaneously, as described in reference to FIGS. 3A-8. The simultaneous detection of various types of electrons is greatly advantageous since the sample location, during simultaneous detection of a number plurality of regions of the image of electrons, is substantially maintained. Additionally, a method for detecting electrons emitted from a sample in a TEM/STEM is provided, comprising measuring the scattering angle of a relatively large amount of electrons scattered from the sample and simultaneously generating multiple images originating from predetermined groups of scattered electron angles. Moreover, the separation between BF detection and DF detection is maintained, such that the standard BF detector can be used in conjunction with the DF detector according to the described embodiments. This is advantageous as, for example, the ability to utilize separate collections schemes for BF and DF enables placing the detectors at different plans of the system, as shown in FIGS. 3A-3D, i.e., the DF detector is at a plan that is closed to the sample than the plan where the BF detector is situated. Also, the characteristics of the BF and DF detectors can be chosen to maximize the performance of each, since the BF detector is separate from the DF detector. Also, as shown in FIG. 3D, by placing the BF detector at a lower plan, i.e., a plan further away from the sample, the BF beam is allowed to expand and can be collected over a wider area.

It is noted that the systems shown in FIGS. 3A-8 may be used in any suitable microscope, such as a SEM with STEM capability, for example.

The detection resolution in a TEM/STEM system may be very high, at an atomic level. To allow sequential detection of more than one region of interest of electrons scattered in different angles, minimal movement of the TEM/STEM system is advisable, so as to ensure that the sample location is the same during detection of the various types of atoms. In standard TEM/STEM systems there may be many mechanisms utilized, such as dampers, for minimizing the mechanical movement of the TEM/STEM system. Therefore, simultaneous detection of a plurality of regions of the image of electrons is advantageous since during this simultaneous imaging the sample location remains substantially the same.

It will be appreciated by persons skilled in the art that the present invention is not limited by what has been particularly shown and described hereinabove. Rather the scope of the present invention includes both combinations and sub-combinations of the various features described hereinabove as well as variations and modifications which would occur to persons skilled in the art upon reading the disclosed embodiments.

The invention claimed is:

1. A High Angle Annular Dark Field (HAADF) detector assembly operating within a Scanning Transmitting Electron Microscope (STEM), provided to detect electrons emitted from a sample that is being scanned by an electron beam, comprising:
   a scintillator comprising an annular scintillating plate having a scintillating surface and a central aperture configured to enable passage of non-scattered electrons, the scintillating surface emitting light signals corresponding to impingement of scattered electrons thereupon;
   a two-dimensional sensor having a light sensing surface and plurality of electrical outputs;
   an optical imaging system configured to form an image of the scintillating surface on the light sensing surface of the two-dimensional sensor by transferring light signals produced in any specific location of the scintillating surface onto a corresponding position on the light sensing surface and thereby maintaining spatial information of the light signals; and, an image processing unit receiving output signals from plurality of electrical outputs of the two-dimensional sensor and providing information of images related to selected positions of the electrons impinging the scintillation surface.

2. The detector assembly of claim 1, wherein the optical imaging system comprises a mirror having an aperture configured for passing non-scattered electrons.

3. The detector assembly of claim 2, further comprising a lens positioned between the mirror and the two-dimensional sensor.

4. The detector assembly of claim 3, further comprising a second lens positioned between the mirror and the scintillator, the second lens having an aperture configured for passing non-scattered electrons.

5. The detector assembly of claim 1, wherein the two-dimensional sensor comprises one of a multi-wire photomultiplier tube or multi-anode photomultiplier tube or multi anode MCP-PMT.

6. The detector assembly of claim 1, wherein the optical imaging system comprises a coherent fiber optic bundle.

7. The detector assembly of claim 1, wherein the two-dimensional sensor comprises n by k sensor elements, and wherein the image processing unit is configured to sample a frame of n×k pixels for each one pixel of the electron beam scan.

8. The detector assembly of claim 7, wherein the image processing unit comprises n×k pre-amplifiers, each coupled to a corresponding one of the n×k sensor elements.

9. The detector assembly of claim 8, wherein the image processing unit comprises N simultaneous outputs, each programmable to provide an output signal corresponding to a group of selected sensor elements.

10. The detector assembly of claim 9, wherein each of the group of selected sensor elements defines an annular ring or a section of an annular ring.

11. The detector assembly of claim 1, wherein the optical imaging system further comprises a variable magnification lens assembly.

12. A High Angle Annular Dark Field detector assembly operating within a Scanning Transmitting Electron Microscope (STEM), comprising:
    an annular electron sensor having a sensing surface configured for sensing scattered electrons passing through a sample and having a central aperture configured to pass non-scattered electrons;
    a sampling unit coupled to the sensing surface and generating a plurality of signals indicating amplitude and spatial location of impinging electrons on the sensing surface; and,
    an image processing unit simultaneously generating a plurality of video signals, each corresponding to a selected group from the plurality of the sensor signals.

13. The detector assembly of claim 12, wherein the sampling unit comprises a two-dimensional light sensor array.

14. The detector assembly of claim 12, wherein each of the plurality of video signals corresponds to a selected scattering angle range of the scattered electrons or selected area on the annular electron sensor.

15. The detector assembly of claim 12, further comprising a variable magnification lens arrangement.

16. A method for detecting electrons emitted from a sample in a scanning transmission electron microscope, comprising:
    using a scintillating plate for detecting electrons scattered from the sample;
    projecting an image of the scintillating plate onto a two-dimensional light sensor and generating a plurality of corresponding signals, each signal indicative of a scattering angle of a scattered electron;
    generating a plurality of signal groups, each signal group being a collection of signals of a user selected scattering angle range;
    converting each of the signal groups into an individual video signal and displaying the video signal on a monitor.

17. The method of claim 16, further comprising allowing non-scattered electrons to pass through an aperture in the scintillating plate.

18. The method of claim 16, further comprising storing the corresponding signals in a computer memory to enable post processing.

19. The method of claim 16, further comprising recording all detected sensor signal for off-line selection and evaluation of various regions of interest.

20. The method of claim 16, wherein projecting an image further comprises varying the magnification of the projected image.

* * * * *